Figure 1:
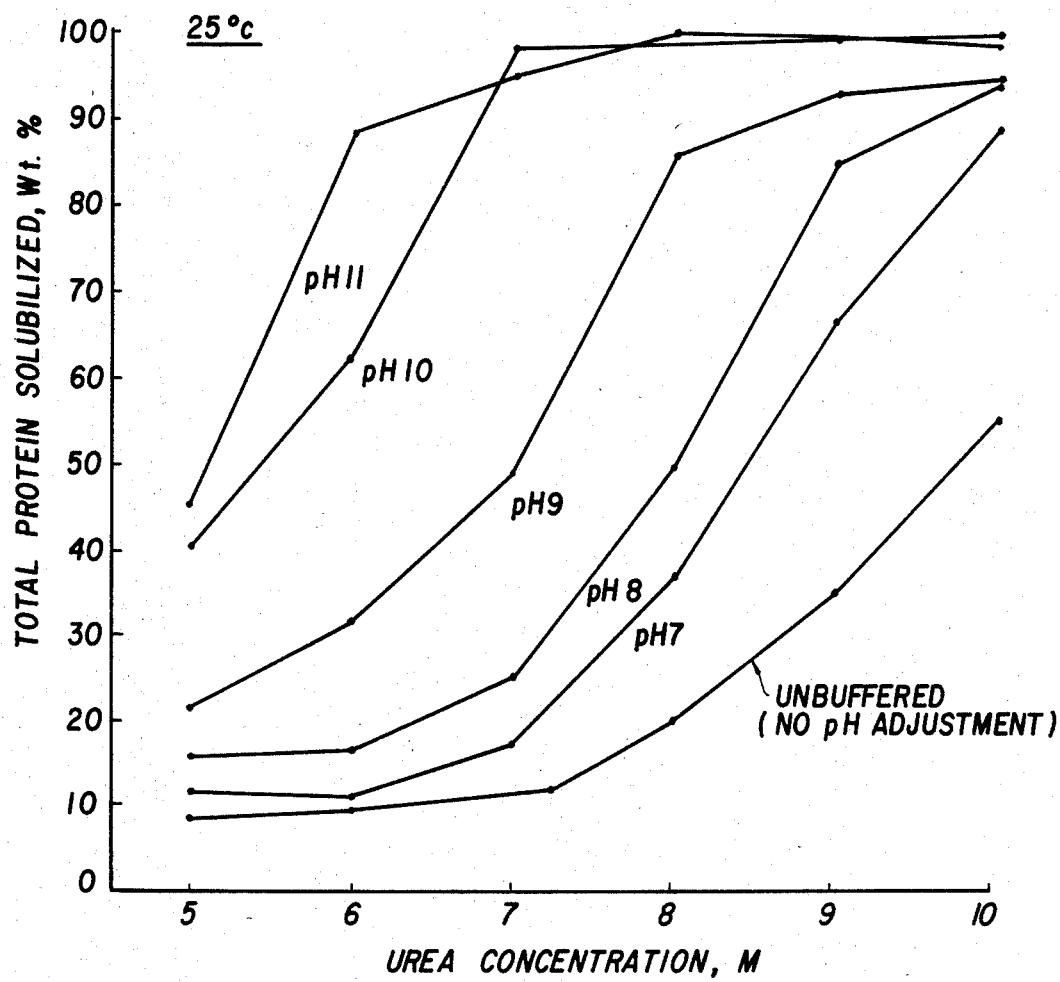

United States Patent [19]

Bentle et al.

[11] Patent Number: 4,652,630

[45] Date of Patent: Mar. 24, 1987

[54] METHOD OF SOMATOTROPIN NATURATION

[75] Inventors: Larry A. Bentle, St. Charles; James W. Mitchell; Stephen B. Storrs, both of St. Louis, all of Mo.

[73] Assignee: Monsanto Company, St. Louis, Mo.

[21] Appl. No.: 704,677

[22] Filed: Feb. 22, 1985

[51] Int. Cl.$^4$ .............................................. C07K 1/02
[52] U.S. Cl. ..................................... 530/344; 530/420
[58] Field of Search ................. 260/112.5 S; 435/253, 435/68; 530/344, 420

[56] References Cited

U.S. PATENT DOCUMENTS 3,845,204 10/1974 Grant ............................ 260/112.5 S

FOREIGN PATENT DOCUMENTS 0114506 1/1984 European Pat. Off. .

OTHER PUBLICATIONS

Lowenstein, "Methods in Enzymology" vol. 13 (1969), 90–99.
Stryer, Biochemistry (1982), 33–35.

*Primary Examiner*—Delbert R. Phillips
*Attorney, Agent, or Firm*—Dennis R. Hoerner, Jr.; J. Timothy Keane; George R. Beck

[57] ABSTRACT

Methods of solubilization and naturation of somatotropin protein from refractile bodies of host cells are disclosed. The solubilization methods embrace the discovery that an aqueous urea solution can be effectively used to solubilize refractile bodies containing such somatotropin protein. Surprisingly, it has been further found that once solubilized, such somatotropin protein can be natured in the urea solution by contacting the solution with a mild oxidizing agent for a time sufficient to result in the formation of the disulfide protein. Naturation can efficiently occur even at high protein concentration, in an impure preparation and in the absence of reducing agent.

24 Claims, 3 Drawing Figures

METHOD OF SOMATOTROPIN NATURATION

Recombinant DNA technology has permitted the expression of heterologous protein in host cells such as *E. coli* bacteria. It has been reported that some heterologous proteins such as the somatotropins (growth hormones) are sequestered, in varying extent following expression, in refractile bodies within the cytoplasm of the host cell.

Chaotropic agents such as guanidine hydrochloride, sodium thiocyanate, urea and various detergents have been used to disrupt the non-covalent intermolecular attractions within proteins. For example, it has been shown that proteins can be "unfolded" by exposing the protein to a chaotropic agent, see Stryer, Biochemistry (2nd edition, 1981) pp 34–35, W. H. Freeman and Company. Likewise, it has been shown that proteins which contain multiple subunits can be dissociated into their respective subunits by exposing the protein to a chaotropic agent.

It has been recently reported in European Patent Application publication number 114,506A that heterologous proteins can be solubilized from refractile bodies using a strong chaotropic agent such as guanidine hydrochloride, detergents such as sodium dodecyl sulfate and salts of thiocyanate. The use of urea, a relatively weak chaotropic agent, to solubilize refractile bodies was reported to be ineffective. Strong denaturants such as guanidine hydrochloride are quite expensive. Moreover, once solubilized in the strong denaturant the heterologous protein must be exchanged into a weak denaturant that will not interfere with downstream ion exchange purification procedures.

Accordingly, it is an object of the present invention to provide improved methods for solubilization and subsequent naturation of heterologous somatotropin proteins from refractile bodies of host cells.

It is an object of the present invention to provide a method which uses a readily available and relatively inexpensive chaotropic agent.

It is another object of the present invention to provide a method in which the naturation step can be conducted at a relatively high somatotropin concentration.

It is yet another object of the present invention to provide a method wherein solubilization and naturation of somatotropin proteins can be carried out in the presence or absence of reducing agent.

It is still another object of the present invention to provide a solubilization method which uses a chaotropic agent that is ecologically safer than agents used in prior methods.

These and other objects and advantages of the present invention will be evident to those skilled in the art from the following description and examples.

DESCRIPTION OF THE INVENTION

Briefly, the present invention provides methods of solubilization and subsequent naturation of somatotropin protein from refractile bodies of host cells. More particularly, the present method embraces the discovery that an aqueous urea solution can be effectively used to solubilize refractile bodies containing such somatotropin protein. Surprisingly, it has been further found that once solubilized, such somatotropin protein can be natured in the urea solution by contacting the solution with a mild oxidizing agent for a time sufficient to result in the formation of the disulfide bonds present in the native conformation of the protein. Naturation can efficiently occur even at high protein concentration, in an impure preparation and in the absence of reducing agent.

For purposes of the present invention, the following terms should be considered to have the definitions listed below.

The term "somatotropin" is meant to include, but not limited to, mammalian somatotropins, such as human, ovine, porcine and bovine somatotropin, and others such as avian somatotropin. In addition to being suitable for the above somatotropin proteins having naturally occurring sequences, the present invention is equally applicable to systems involving analogs and homologs of the naturally occurring protein having somatotropin-like bioactivity. It will be understood by those skilled in the art that other somatotropinlike proteins having similar chemical properties such as prolactin and placental lactogen are considered for purification purposes substantially equivalent to somatotropins. Accordingly, to the extent that such proteins are equivalents for purification purposes the present invention includes such proteins.

"Heterologous" proteins are proteins which are normally not produced by the host cell. Recombinant DNA technology has permitted the expression of relatively large amounts of heterologous proteins from transformed host cells. However, while not fully understood, these foreign proteins are often sequestered in insoluble light refractile bodies in the cytoplasm of the host cell.

By "refractile bodies" is meant the inclusion bodies or cytoplasmic aggregates containing, at least in part, the heterologous somatotropin to be recovered. These aggregates appear as bright spots under a phase contrast microscope.

By "host cell" is meant a microbial cell such as bacteria and yeast or other suitable cells such as animal and plant cells which has been transformed to express the heterologous somatotropin. Host cells which are contemplated by the present invention are those in which the heterologous somatotropin is sequestered following expression in refractile bodies. An exemplary host cell is *E. coli* K12 (strain W3110/pBGH-1) which has been transformed to permit expression of bovine somatotropin.

"Naturation" refers to the folding and oxidation of the somatotropin protein to its native conformation to ensure biological activity.

"Folding" refers to the return of the overall conformational shape of the protein sufficient to permit proper oxidation. Folding is accomplished by reducing the denaturing effect of the urea by adjusting the urea concentration to a suitable level, if necessary, to permit the amino acids sequence of the protein to interact and assume its native secondary and tertiary structure.

"Oxidation" refers to the formation of the intramolecular disulfide bonds to obtain the stable native conformation to ensure biological activity.

By "mild oxidizing agent" is meant an agent which promotes the oxidation of the sulfhydral groups thereby forming the intramolecular disulfide bonds while not oxidizing other substituent groups of the subject protein. While mild agents such as hydrogen peroxide may be used, exposure to air is quite acceptable and is preferred.

By "biological activity" is meant that the somatotropin is capable of effecting its intended in vivo physiological response. The biological activity can be determined in the absence of in vivo testing in the particular species by carrying out suitable bioassays. A suitable bioassay for the somatotropins embraced by this invention is the "rat weight gain biossay". In this bioassay the bioactivity of somatotropin preparations are assessed relative to a known preparation (i.e. extracted native somatotropin) by relating the amount of weight gain of hypophysectomized rats to varying amounts of administered preparation.

Somatotropins are hormones which are secreted by the adenohypophysis (anterior lobe of the pituitary gland) and are known to affect the rate of skeletal growth and gain in body weight. Administration of somatotropin has been shown to cause an increase in milk production in lactating animals such as dairy cows and goats. Typically, somatotropins contain approximately 191 amino acid residues and have an approximate molecular weight of 22,000 daltons. The complete amino acid sequences have been established for somatotropins from several species, including humans and animals such as birds (avian), sheep (ovine), pig (porcine) and cattle (bovine). A comparison of the amino acid sequence from the species listed above indicates a relatively high overall homology when considering "conservative" amino acid replacements. In general terms, some "conservative" substitutions can occur without substantial change in the gross chemical properties of a protein. Exemplary of such substitution are substitution of aliphatic hydrophobic residues for one another (isoleucine, valine, leucine and methionine) and substitution of polar residues for one another (arginine for lysine, glutamine for asparagine and glutamic acid for aspartic acid). Ionic residues of opposite charge have been shown to substitute for one another, for example, aspartic acid or glutamic acid for lysine. Moreover, substitutions that are "radical" (representing different kinds of side chains) can occur without substantial change in function or chemical properties when the locus of substitution is not critical for conformation and the degree of substitution is not extensive.

In Table I below is shown the reported primary configuration for somatotropins of various animal species. The following abbreviations are used in Table I: BGH (bovine somatotropin); PGH (porcine somatotropin, i.e., pig); OGH (ovine somatotropin, i.e., sheep); AGH (avian stomatotropin, i.e., poultry); HGH (human somatotropin). The symbol "X" denotes a spare in the sequence, inserted only to demonstrate the alignment of the representative somatotropins. Numbering in a particular sequence would eliminate this insertion. For example, in BGH position 126 is Leu.

TABLE I
Amino Acid Sequences for Representative Somatotropins

```
                1                               10                                      20
BGH   Phe—Pro—Ala—Met—Ser—Leu—Ser—Gly—Leu—Phe—Ala—Asn—Ala—Val—Leu—Arg—Ala—Gln—His—Leu—
PGH   ---------------Pro-----------Ser-------
OGH   ------------------------------------------
AGH   ---------------Pro-----------Asn-----------
HGH   ------Thr—Ile—Pro-------Arg--------Asp-------Met----------His—Arg------

30                                      40
BGH   His—Gln—Leu—Ala—Ala—Asp—Thr—Phe—Lys—Glu—Phe—Glu—Arg—Thr—Tyr—Ile—Pro—Glu—Gly—Gln—
PGH   ----------------------Tyr--------------------Ala--------
OGH   ------------------------------------------
AGH   ------Leu----------Gln------Tyr-----------------------Asp------
HGH   ------------Phe-----------Tyr—Gln----------Glu—Ala----------Lys—Glu------

50                                      60
BGH   Arg—Tyr—Ser—X—Ile—Gln—Asn—Thr—Gln—Val—Ala—Phe—Cys—Phe—Ser—Glu—Thr—Ile—Pro—Ala—
PGH   ----------------Ala------Ala---------
OGH   ------------------------------------------
AGH   ------Thr------Asn—Lys------Ser------Ala-----------Tyr----------
HGH   Lys-----------Phe—Leu----------Pro---------Thr—Ser—Leu-----------Ser----------Thr- 70                                      80
BGH   Pro—Thr—Gly—Lys—Asn—Glu—Ala—Gln—Gln—Lys—Ser—Asp—Leu—Glu—Leu—Leu—Arg—Ile—Ser—Leu—
PGH   -----------Asp--------------Arg----------Val--------------Phe--------
OGH   ------------------------------------------
AGH   ------Asp—Asp------------Met—Gly-----------Phe---------
HGH   ------Ser—Asn—Arg—Glu----------Thr-------------Asn---------Gln------

90                                      100
BGH   Leu—Leu—Ile—Gln—Ser—Trp—Leu—Gly—Pro—Leu—Gln—Phe—Leu—Ser—Arg—Val—Phe—Thr—Asn—Ser—
PGH   --------------------Val---------
OGH   ------------------------------------------
AGH   Val-----------Thr---------Val---------Tyr-----------Lys-----------Asn-
HGH   -------------------Glu---------Val-----------Arg—Ser-----------Ala---------

110                                     120
BGH   Leu—Val—Phe—Gly—Thr—Ser—Asp—Arg—X—Val—Tyr—Glu—Lys—Leu—Lys—Asp—Leu—Glu—Glu—Gly—
PGH   ------------------------------------------
OGH   ------------------------------------------
AGH   -----------------------Phe---------
HGH   ------Tyr---------Ala---------Asn—Ser—Asp-----------Asp—Leu---------

130                                     140
BGH   Ile—Leu—Ala—Leu—Met—Arg—Glu—Leu—Glu—Asp—Gly—Thr—Pro—Arg—Ala—Gly—Gln—Ile—Leu—Lys—
PGH   ------Gln----------------Ser-----
OGH   -------------------Val---------
AGH   ------Gln---------Arg—Ser-----------Gly—Pro---------Leu---------Arg-
HGH   ------Gln—Thr----------Gly—Arg---------------Ser-----------Thr---------Phe---------
```

TABLE I-continued
Amino Acid Sequences for Representative Somatotropins

```
                              150                                                    160
BGH  Gln—Thr—Tyr—Asp—Lys—Phe—Asp—Thr—Asn—Met—Arg—Ser—Asp—Asp—Ala—Leu—Leu—Lys—Asn—Tyr—
PGH  ----------------------------------------Leu----------------------------------------
OGH  ------------------------------------------------------------------------------------
AGH  Pro-----------------------------Ile—His—Leu----------Asn—Glu-----------------------
HGH  -----------Ser----------------------------Ser—His—Asn-----------------------------

170                                                    180
BGH  Gly—Leu—Leu—Ser—Cys—Phe—Arg—Lys—Asp—Leu—His—Lys—Thr—Glu—Thr—Tyr—Leu—Arg—Val—Met—
PGH  --------------------Lys-------------------Ala-------------------------------------
OGH  ----------------------------------------------------------------------------------
AGH  --------------------Lys-----------------------Val-----------------------Lys-------
HGH  -----------Tyr----------------------Met—Asp--------Val-------Phe---------------Ile—Val-

190
BGH  Lys—Cys—Arg—Arg—Phe—Gly—Glu—Ala—Ser—Cys—Ala—Phe—
PGH  ------------------Val---------Ser---------------
OGH  -------------------------------------------------
AGH  -----------------------------Ser—Asn---------Thr—Ile-
HGH  Gln---------X------------Ser—Val----------Gly--------------Gly---------
```

A tabulation of the relative amounts of particular amino acids, based on the reported sequences, is provided below in Table II.

TABLE II
Amino Acid Composition of Representative Somatotropins

| Amino Acid | Human | Bovine | Ovine | Porcine | Avian |
|---|---|---|---|---|---|
| Aspartic Acid | 11 | 10 | 10 | 10 | 11 |
| Asparagine | 9 | 6 | 6 | 5 | 9 |
| Threonine | 10 | 12 | 12 | 8 | 11 |
| Serine | 18 | 13 | 13 | 15 | 11 |
| Glutamic Acid | 14 | 13 | 13 | 13 | 12 |
| Glutamine | 13 | 11 | 11 | 12 | 10 |
| Proline | 8 | 6 | 6 | 7 | 9 |
| Glycine | 8 | 10 | 9 | 8 | 7 |
| Alanine | 7 | 14 | 14 | 17 | 12 |
| Valine | 7 | 6 | 7 | 7 | 8 |
| Methionine | 3 | 4 | 4 | 3 | 4 |
| Isoleucine | 8 | 7 | 7 | 6 | 6 |
| Leucine | 26 | 27 | 27 | 26 | 26 |
| Tyrosine | 8 | 6 | 6 | 7 | 8 |
| Phenylalanine | 13 | 13 | 13 | 13 | 11 |
| Histidine | 3 | 3 | 3 | 3 | 4 |
| Lysine | 9 | 11 | 11 | 11 | 14 |
| Arginine | 11 | 13 | 13 | 12 | 12 |
| Trytophan | 1 | 1 | 1 | 1 | 1 |
| Cysteine | 4 | 4 | 4 | 4 | 4 |

Disulfide bridges in somatotropin proteins are reported to be homogeneously two in number. It is now well supported in the literature that mammalian somatotropins form a relatively homogeneous family of proteins.

It has been reported that most heterologous proteins expressed in E. coli bacteria are sequestered, in varied extent following expression, in refractile bodies within the cytoplasm of the bacteria. While not fully understood, this is believed to result, at least in part, from the overproduction of the heterologous protein in the host cell. Heterologous somatotropins are believed to be present in the refractile bodies in substantially reduced form (without disulfide linkages) due to the relatively high redox potential of the E. coli cell.

Numerous somatotropins have been expressed in E. coli bacteria. For example, human somatotropin (E. coli K12 strain W3110/p107) as disclosed in U.S. Pat. No. 4,342,832; bovine somatotropin (E. coli K12 strain W3110/pBGH-1) as disclosed in European Patent Application Publication No. 75,444A (U.S. Appln. Ser. No. 303,689, filed 9/18/81); porcine somatotropin as disclosed in European Patent application Publication No. 111,389A (U.S. Appln. Ser. No. 439,977, filed 11/8/1982); and avian somatotropin as disclosed in PCT Application Publication Number W084/01150 filed Sept. 13, 1983.

For purposes of the present invention, refractile bodies can be recovered using standard biological techniques. For example, the host cell, previously killed with a solution 0.25 weight percent in both toluene and phenol can be disrupted by commonly used mechanical means such as a Manton-Gaulin homogenizer or French press. It is preferred that the disruption process is conducted such that cellular debris from the host organism is sufficiently disrupted such that it fails to sediment from the homogenate solution under low speed centrifugation. Under low speed centrifugation, the refractile bodies sediment from the homogenate solution. The refractile bodies are preferably resuspended, washed and centrifuged again. The supernatant is discarded yielding a substantially pure preparation. Although not critical to the practice of the present invention, it is preferred that the refractile body preparation be homogenized again to ensure a freely dispersed preparation devoid of agglomerated refractile bodies. The preparation is preferably homogenized in a Manton-Gaulin homogenizer at 3000–5000 psig.

It has been found that somatotropin proteins can be efficiently solubilized from refractile bodies of the host cell by subjecting the refractile bodies to an effective amount and concentration of urea, a weak chaotropic agent. It will be evident from the discussion below that urea is an effective solubilizing agent at particular concentrations and pH. The concentration and absolute amount of urea needed will depend on the pH, the particular somatotropin, and amount of protein to be solubilized. The use of urea is economically favored since it is readily available, relatively inexpensive, ecologically safer than stronger chaotropic agents and does not substantially interfere with the downstream purification procedures.

Refractile bodies of E. coli containing somatotropin proteins were solubilized in varying extent in an aqueous solution containing between about 8M and 10M urea at near neutral pH. Only partial solubilization of relatively small quantities of an essentially pure refractile body preparation is obtained with urea at near neutral pH within a short time. As the urea concentration is decreased the extent of solubilization decreases. At a urea concentration much below about 8M and near neutral pH little solubilization can be detected.

Hydrophobic proteins are, in general, more soluble in aqueous solution at reduced temperatures. With respect to the present invention, it was found that solubilization of the somatotropin-like proteins by urea was greater at reduced temperatures, typically 4° C., than at room temperatures, typically 20° C.–25° C. In addition to greater solubility, solubilization at reduced temperatures results in increased stability of the urea solution and inhibition of protease activity which may be present in the refractile body preparation. While the advantageous effects described above have been shown to result from operating at reduced temperatures, such operation is not critical to the present invention. Rather, one may choose other temperatures as long as the protein is not irreversibly denatured. However, in most cases it is expected that temperatures below 25° C. but above the freezing point of the solution will be most advantageous and are therefore preferred.

In the present invention solubilization of significant quantities of somatotropin protein was attained by increasing or decreasing the pH of the aqueous urea solution. While the unexpected effect of adjusting the solution pH to a more acidic or alkaline pH will be evident from the following examples, adjustment to an alkaline pH is preferred since the naturation step, specifically the oxidation of the reduced monomer, is base catalyzed. The pH of the solution may be made more alkaline by addition of a suitable base such as sodium hydroxide. As the refractile bodies dissolve, the pH of the solution may decrease, requiring the periodic addition of more base to maintain alkaline conditions. Refractile bodies have been completely solubilized at concentrations as high as 60 mg/ml or more. Moreover, solubilization has been achieved at urea concentrations as low as 1.0M. The solubilization conditions required (i.e., urea concentration, amount of urea solution used relative to the amount of refractile bodies and the solution pH) will depend on the particular refractile body composition and the amount of refractile bodies to be solubilized.

Although not critical to the present invention, one may employ a suitable non-interfering buffering agent to aid in dampening shifts in solution pH during the solubilization step. Suitable buffering agents include, but are not limited to, Tris(hydroxymethyl)aminomethane and ethanolamine. Tris(hydroxymethyl)aminomethane, hereinafter referred to as "Tris", is preferred, since it is inexpensive and readily available. Tris concentrations between about 10 and 90 mM appear to not significantly affect somatotropin yield. A freshly prepared 50 mM Tris solution has a pH of about 11.5. However, Tris, with a pK of 8.8 at 4° C., has only weak buffering capacity at this high pH. A Tris concentration between about 40 and 60 mM is preferred to minimize Tris usage while still maintaining some buffering capacity.

If the somatotropin is present in the refractile bodies in aggregated and/or oxidized form, it is preferred to have an exogenous reducing agent such as a $\beta$-mercaptoethanol or 1,4-dithiothreitol in the aqueous urea solution to promote cleavage of the intramolecular and intermolecular disulfide bonds. If such incorrectly folded monomer or aggregated somatotropin is present, the presence of reducing agent will typically enhance the recovery of biologically active somatotropin. It has been found that the reducing agent and the sulfhydral groups can oxidize concomitantly in the urea solution giving a good yield of correctly oxidized monomeric somatotropin and does not necessarily have to be removed prior to oxidation of the subject somatotropin. In the case of N-methionyl bovine somatotropin and N-methionyl porcine somatotropin expressed in an E. coli host cell it was found that the protein was sequestered in the refractile bodies in substantially reduced form (no disulfide linkages). Hence, for these preparations the use of reducing reagents was unnecessary.

In another aspect of the present method, it has been further found that once solubilized, such somatotropins can be easily transformed to their native form. In their native form, somatotropins contain two intramolecular disulfide bonds between four cysteine residues. Unfortunately, when undergoing oxidation from the reduced form the cysteine residues may combine to form two intramolecular bonds in any one of three ways only one combination of which defines the native form. Likewise, cysteine residues from one somatotropin molecule may form disulfide bonds with cysteine residues from another molecule producing dimers, trimers and higher oligomers. The ratio of correctly formed monomer to incorrectly formed monomer and oligomers is influenced by the conditions under which the somatotropin protein is folded and oxidized.

Prior to the present discovery, it was standard biochemical practice when naturing protein to exchange the protein from the denaturing solution (i.e., chaotropic solution) to an acceptable buffer solution such as sodium bicarbonate at a pH suitable for the particular protein in the presence of a reducing reagent, see Stryer, Biochemistry (2nd edition, 1981) pp 32-35, W. H. Freeman and Company and Bewley et al., "Human Pituitary Growth Hormone—The Reduction and Reoxidation of the Hormone", *Archives of Biochemistry and Biophysics*, 138, pp 338-346 (1970). The volume of buffer solution utilized was such that the protein concentration was quite low, usually less than about 1.5 mg/ml. Oxidation of the protein was then accomplished by exposing the solution to air.

Formation of disulfide bonds in proteins is proposed to occur by a base catalyzed free radical mechanism such as that described by March in Adv. Organic Chemistry, McGraw Hill (1977). Being base catalyzed, the oxidation step is preferably carried out at alkaline pH. While the oxidation reaction forming the disulfide bonds will proceed at pH greater than about 7, an operating pH above the pK for a protein sulfhydral group ($\sim$8.4) is preferred. Specifically, an operating pH between about 9 and 12 is preferred. If a buffer is used, Tris(hydroxymethyl)amino methane is preferred.

Contrary to prior practice, it has now been found that somatotropins can be efficiently natured while still dissolved in the urea solution by contacting the solution with a mild oxidizing agent such as hydrogen peroxide or air for a sufficient time to oxidize the sulfhydral groups forming intramolecular disulfide bonds. It has been further found that naturation can be carried out at somatotropin concentrations as high as 30 mg/ml or more, but preferably less than about 30 mg/ml and more preferably less than about 20 mg/ml. Naturation proceeds in an efficient manner in the presence of contaminating proteins of the host cell in the presence or absence of reducing reagents. The amount of somatotropin monomer may be determined by any suitable biochemical techniques such as radioimmuneassay (RIA), size exclusion chromatography and high performance liquid chromatography (HPLC).

In the absence of exogenous reducing agents such as β-mercaptoethanol and 1,4 dithiothreitol or precautions to exclude oxygen, oxidation of the somatotropin molecule begins upon solubilization. Urea concentration appears to be the most influential parameter affecting the yield of biologically active somatotropin monomer. Indeed, oxidation will occur at substantially any urea concentration at which the somatotropin will remain solubilized. It should be understood that once solubilized, somatotropins will remain in solution at reduced temperatures at urea concentrations of 1M or lower. Hence, to maximize production of such monomer one should adjust the urea concentration from that utilized in the solubilization step to that determined to be optimal for the renaturation step. The particular optimal concentration will necessarily depend on the particular somatotropin. When it is desirable to reduce the urea concentration following solubilization, dilution may be accomplished by addition of distilled water or buffer solution. One may choose to use reducing agent to temper the need for prompt action on adjustment of the urea concentration. In the absence of reducing agent, monomer yield decreases for MBS approximately 5 wt% for each hour lapsed prior to dilution of the urea concentration when 7.5M urea is used for solubilization.

In the case of N-methionyl bovine somatotropin, a urea concentration during naturation of between about 4M and 5M is preferred. Naturation appears optimal at about 4.5M with decreased monomer recovery and increased aggregate formation at both higher and lower urea concentrations. Accordingly, if 7.5M urea is used for solubilization, rapid dilution to 4.5M urea with distilled water or a suitable buffer such as Tris is preferred in the absence of reducing agent to minimize oxidation at the higher non-optimal urea concentration.

In the case of N-methionyl porcine somatotropin, which differs from MBS in 18 amino acids, a urea concentration during reactivation of between 2.5M and 3.5M is preferred. Naturation appears optimal at about 3M urea with decreased monomer recovery and increased aggregate formation at both higher and lower urea concentrations. Likewise, rapid dilution from 7.5M to 3M urea with good mixing, a suitable buffer such as Tris is preferred in the absence of reducing agent to minimize renaturation at higher non-optimal urea concentrations.

Somatotropins solubilized and natured in the above-described manner were subsequently purified by standard chromatographic techniques. Bioactivity was indicated by positive response to rat growth bioassay tests. In this assay, the bioactivity of the heterologous somatotropin is assessed relative to a known lot of somatotropin material (e.g., bovine or porcine pituitary somatotropin) by relating the amount of weight gain demonstrated by hypophysectomized rats to varying amounts of administered material. Regression slopes of body weight gain versus dosages administered for the particular somatotropin material are compared to the known standard (i.e., pituitary material) and a relative bioactivity in U(units)/mg growth hormone calculated for the heterologous somatotropin material.

N-methionyl bovine somatotropin solubilized and natured in the method embraced by the present invention and subsequently purified was subsequently administered to dairy cows. Dairy cows administered such a preparation produced 10% to 40% (by weight) more milk than control animals, see Eppard et al. "The Effect of Long-term Administration of Growth Hormone on Performance of Lactating Dairy Cows", Proceedings of the 1984 Cornell Nutrition Conference.

The following examples are included to better elucidate the practice of the present invention. It should be understood that these examples are included for illustrative purpose only and are not, in any way, intended to limit the scope of the present invention.

EXAMPLE 1

The present invention has been demonstrated by the solubilization of N-methionyl bovine somatotropin (MBS) expressed in E. coli as generally described in Seeburg et al., DNA 2(1): 37-45 (1983). Details for the individual steps can be found in Goeddel et al., Nature Vol 281 (October, 1979); DeBoert et al., Promoters: Structure and Frunction, pp 462–481 Praeger Scientific Publishing Co., (1982); and Miozzari et al., J. Bacteriology Vol 133, pp 1457–1466 (1978). Harvested cells were disrupted by double passage through a Manton Gualin homogenizer. Refractile bodies, containing MBS, were pelleted from the homogenate solution under low speed centrifugation. The supernatant was discarded, refractile bodies resuspended, washed and again pelleted. The supernatant was again discarded leaving a substantially pure refractile body preparation.

Refractile bodies prepared in the manner described above were subjected to various concentrations of an aqueous urea solution at various pH levels at 25° C. All buffered solutions contained 100 mM Tris-base. pH adjustment was accomplished by addition of HCl. The final refractile body concentration was about 4 mg/ml of solution. The extent of dissolution was determined spectrophotometrically assuming the refractile bodies were totally proteinaceous and using an extinction coefficient ($\epsilon$) of 0.68 at 277 nm and 1 cm. path length, as indicative of a protein concentration of 1 mg/ml. The starting concentration was determined spectrophotometrically for a completely dissolved sample. The results of the above described experiment are illustrated in FIG. 1. This data supports the unexpected discovery that adjustments of the pH to alkaline conditions substantially enhances the degree of solubilization.

EXAMPLE 2

Figure 2:
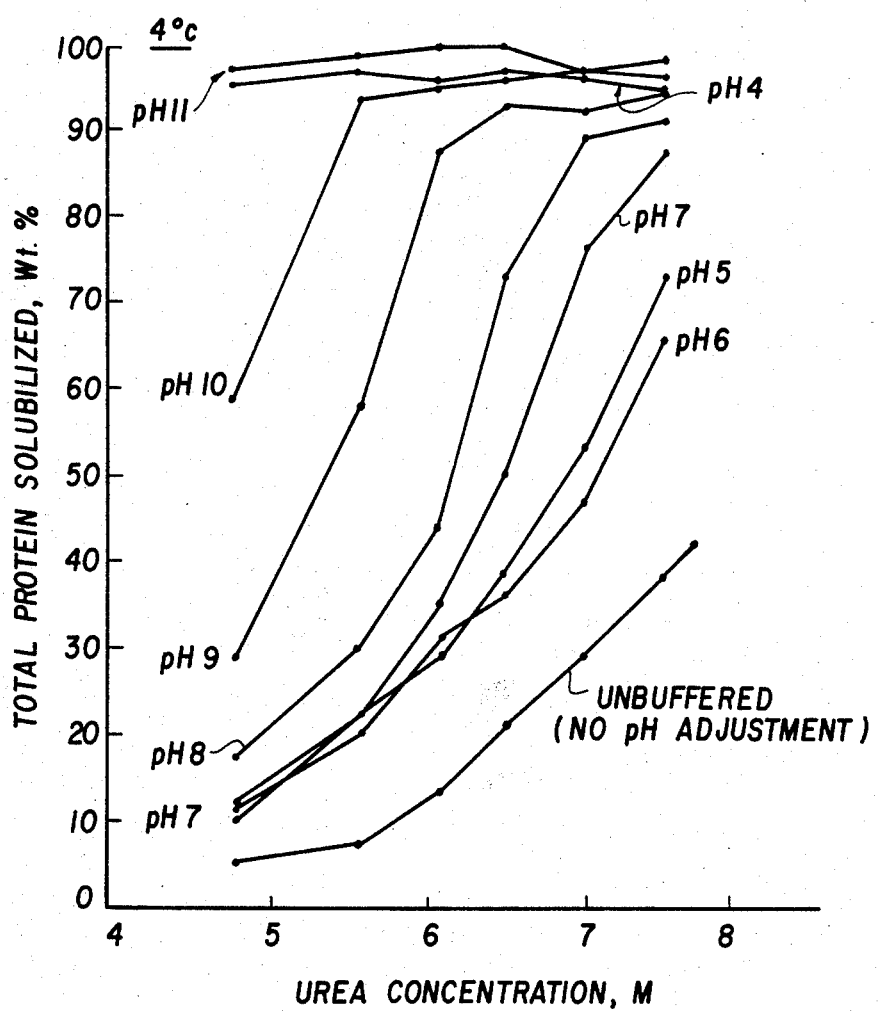

The procedure described in Example 1 was followed except that the temperature was maintained at 4° C. and the pH was adjusted to both acidic and alkaline levels. As on Example 1, all buffered solutions contained 100 mM Tris-base. pH adjustment to acidic levels was accomplished by addition of acetic acid. The results of this experiment are illustrated in FIG. 2. Comparing FIGS. 1 and 2 at constant urea concentration and a given pH will show the solubilization enhancement obtained at reduced temperatures (4° C.) compared to that at room temperatures (25° C.).

COMPARATIVE EXAMPLE A

Refractile bodies containing MBS were prepared in the manner described in Example 1. Refractile bodies were admixed with a 10M urea solution without pH adjustment such that the final refractile body concentration was about 5.0 mg/ml. The solution was mixed and allowed to equilibrate overnight at 4° C. The degree of solubilization was determined to be only about 2.9 mg/ml by the spectrophotometric method described above. The starting concentration of refractile bodies was determined by adding enough urea solution to completely dissolve the refractile bodies spectrophotometrically measuring the completely dissolved solution and adjusting for dilution.

COMPARATIVE EXAMPLE B

Refractile bodies containing MBS, prepared in the manner described in Example 1, were admixed with an aqueous 8.0M urea solution without pH adjustment such that the final refractile body concentration was about 5.0 mg/ml. The solution was mixed and allowed to equilibrate overnight at 4° C. The degree of solubilization was determined to be about 2.4 mg/ml by the spectrophotometric method described above. The starting concentration of refractile bodies was determined by adding enough urea solution to completely dissolve the refractile bodies spectrophotometrically measuring the completely dissolved solution and adjusting for dilution.

EXAMPLE 3

Refractile bodies containing MBS, prepared in the manner described in Example 1, were admixed with an unbuffered aqueous 4.5M urea solution such that the refractile body concentration was about 66 mg/ml. The solution pH was adjusted from pH 7 to pH 11 with dilute NAOH. The solution clarified indicating complete solubilization. The refractile body concentration was determined to be 66 mg/ml by spectrophotometric analysis described in Example 1.

EXAMPLE 4

Figure 3:
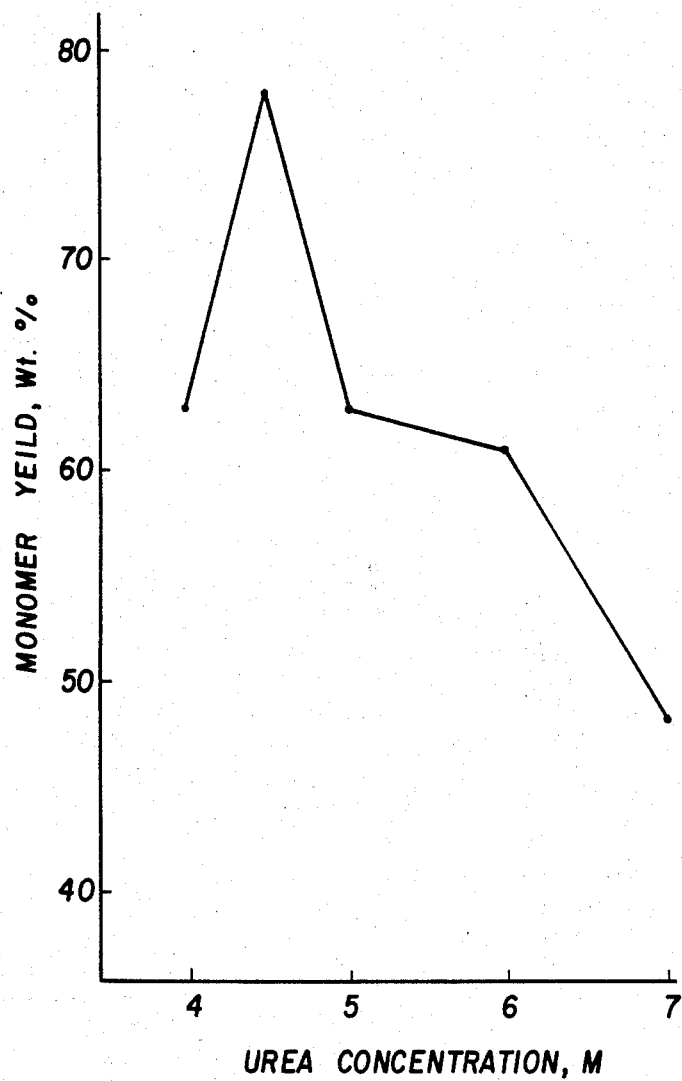

Refractile bodies containing MBS, prepared in the manner described in Example 1, were solubilized in an aqueous 7.5M urea solution containing 100 mM TRIS at pH 10.5. The urea concentration was adjusted to various levels by adding 100 mM TRIS and the total protein concentration maintained at about 1 mg/ml (determined by spectrophotometric analysis of a completely dissolved sample) by addition of a volume of the appropriate urea solution. The dissolved MBS was permitted to oxidize by exposing the solution to air under stirred conditions for a twenty-four hour period. The results are graphically illustrated in FIG. 3. MBS monomer yield is indicated as a weight percent of total MBS content. As shown in FIG. 3, optimal naturation efficiency is obtained at a urea concentration of about 4.5M.

EXAMPLE 5

Following the procedure described in Example 4, refractile bodies containing MBS were solubilized in an aqueous 7.5M urea solution having 100 mM TRIS at pH 10.5. Following solubilization, the solution was diluted to 4.5M urea with 100 mM Tris and the pH adjusted to levels between 10.5 and 8.5. These individual trials were permitted to oxidize by exposure to air under stirred conditions for 24 hours. MBS monomer and oligomer content was determined by HPLC. While the results indicate a relatively flat response in naturation efficiency versus solution pH during oxidation, there is a trend toward higher efficiency at higher pH. In addition, the base catalyzed oxidation proceeds faster at the more alkaline pH.

EXAMPLE 6

Approximately 150 ml of a refractile body preparation, prepared in the manner described in Example 1, was added to about 850 ml of an aqueous 5.3M urea solution at 4° C. The resulting 4.5M urea solution was adjusted to pH 11 with 50 wt % NaOH solution. The refractile bodies completely dissolved resulting in a total MBS concentration of about 12.4 mg/ml. The solution was stirred at 4° C. overnight to oxidize the MBS. HPLC analysis of the oxidized solution indicated an MBS monomer yield efficiency of about 80 wt%.

EXAMPLE 7

N-methionyl porcine somatotropin (MPS) was expressed in $E.\ coli$ using the general teachings of the references listed in Example 1. Following recovery of the refractile bodies containing the MPS using the method previously described, they were solubilized at 4° C. in 7.5M urea, 90 mM Tris pH 11.0. One hundred thirteen mg of refractile body pellet (wet wt.) were dissolved per milliliter of the above urea solution. Samples were diluted with 90 mM Tris and/or urea to obtain urea concentrations of 4.5M, 3.0M and 2.0M with an MPS concentration of 4 mg/ml based on the wet weight of the refractile body pellet. The samples were permitted to oxidize by exposure to air overnight under stirred conditions. Assay by HPLC indicated an optimal MPS monomer yield at a urea concentration of 3M.

EXAMPLE 8

Following the procedure outlined in Example 7, MPS was solubilized at 4° C. in aqueous 7.5M urea, 90 mM Tris at pH 11 at three different concentrations (20, 40 and 80 mg pellet (wet wt.) per ml of the above urea solution). Samples of the solutions were diluted with 90 mM Tris and/or urea to obtain a urea concentration of 3M and MPS concentrations of 1 mg/ml. Diluted MPS solutions were exposed to air under stirred conditions at 4° C. for 56 hours. Assay by HPLC indicated an average MPS monomer yield of 69 wt%.

EXAMPLE 9

The procedure of Example 8 was followed except solubilization and naturation was performed in the presence of 0.1 mM 1,4-dithiothreitol. Assay by HPLC indicated an average MPS monomer yield of 66 wt%.

EXAMPLE 10

Three variants of BGH, namely $Ala_{-1}$, $Ala_{-1}V_{126}$ and $Met_{-1}Val_{126}$, were expressed in $E.\ coli$ following the procedures described in a concurrently filed and commonly assigned U.S. patent application by G. G. Krivi entitled "Production of Proteins in Procaryotes", specifically incorporated herein by reference. The BGH variants were solubilized and natured following the general procedures described in Example 1.

Refractile bodies containing the respective BGH variant were recovered as described in Example 1. Approximately 300 grams (wet wt.) of refractile bodies were suspended in water to yield a 1 liter slurry. This slurry was added to about 5 liters of 9M urea, 108 mM Tris resulting in a solubilization solution comprising the respective BGH variant in 7.5M urea and 90 mM Tris at pH 10.5 and 4° C. Complete solubilization occurred after stirring for a few minutes. Four liters of cold water were slowly added to yield a naturation solution comprising the respective BGH variant in 4.5M urea, 54 mM Tris at pH 10.5 and 4° C. The solution was stirred and the respective BGH variant permitted to oxidize by exposing the solution to air for about 48 hours. The oxidized BGH variant solutions were assayed by HPLC indicating a monomer yield of about 60-70 wt% for all three BGH variants.

EXAMPLE 11

The structural homology of somatotropin protein obtained as described above to that of the natural pituitary somatotropin was determined by circular dichromism as described by Bewley, *Recent Progress in Hormone Research*, Vol. 35 pp 155-210, Academic Press. Specifically, MBS and the Ala$_{-1}$ variant of BGH was compared to bovine pituitary somatotropin. Samples were dissolved in a 50 mM sodium bicarbonate, pH 9.5, and analyzed by the above-described technique. The results of this analysis confirm that the recombinant somatotropin prepared in the manner described herein was in its native conformation following naturation.

We claim:

1. A method for solubilization and naturation of somatotropin protein from refractile bodies of a host cell containing said protein, which method comprises contacting said bodies with an effective amount and concentration of an aqueous urea solution at a pH effective to accomplish solubilization of said protein and then contacting the solution containing said protein with a mild oxidizing agent for a time sufficient to form intramolecular disulfide bonds between cysteine residues contained in said somatotropin protein.

2. The method of claim 1 in which the naturation is conducted in a urea concentration between about 3 and 5M.

3. The method of claim 1 in which the naturation is conducted at a pH above 9.

4. The method of claim 1 in which the naturation is conducted at a pH between about 9 and 12.

5. The method of claim 1 in which the naturation is conducted at a temperature above the freezing point of the solution and below about 25° C.

6. The method of claim 1 in which the naturation is conducted in the presence of reducing agent.

7. The method of claim 1 in which the naturation is conducted in the absence of reducing agent.

8. The method of claim 1 in which the somatotropin is bovine or porcine somatotropin.

9. The method of claim 8 in which the naturation is conducted at a urea concentration between about 3 and 5M; a temperature above the freezing point of the solution and below about 25° C.; and a pH between about 9 and 12.

10. A method for naturation of somatotropin protein which comprises contacting a urea solution of said protein with a mild oxidizing agent for a time sufficient to form intramolecular disulfide bonds between cysteine residues contained in said somatotropin protein, said naturation conducted in a urea concentration between about 3 and 5M.

11. The method of claim 10 in which the naturation is conducted at a pH above 9.

12. The method of claim 10 in which the naturation is conducted at a pH between about 9 and 12.

13. The method of claim 10 in which the naturation is conducted at a temperature above the freezing point of the solution and below about 25° C.

14. The method of claim 10 in which the naturation is conducted in the presence of reducing agent.

15. The method of claim 10 in which the naturation is conducted in the absence of reducing agent.

16. The method of claim 10 in which the somatotropin is bovine or porcine somatotropin.

17. The method of claim 16 in which the naturation is conducted at a temperature above the freezing point of the solution and below about 25° C., and at a pH between about 9 and 12.

18. A method for naturation of somatotropin protein which comprises contacting a urea solution of said protein with a mild oxidizing agent for a time sufficient to form intramolecular disulfide bonds between cysteine residues contained in said somatotropin protein, said naturation conducted at a pH above 9.

19. The method of claim 18 in which the naturation is conducted at a pH between about 9 and 12.

20. The method of claim 18 in which the naturation is conducted at a temperature above the freezing point of the solution and below about 25° C.

21. The method of claim 18 in which the naturation is conducted in the presence of reducing agent.

22. The method of claim 18 in which the naturation is conducted in the absence of reducing agent.

23. The method of claim 18 in which the somatotropin is bovine or porcine somatotropin.

24. The method of claim 23 in which the naturation is conducted at a urea concentration between about 3 and 5M, and a temperature above the freezing point of the solution and below about 25° C.

* * * * *

REEXAMINATION CERTIFICATE (1833rd)
United States Patent [19]
Bentle et al.

[11] B1 4,652,630
[45] Certificate Issued Nov. 3, 1992

[54] METHOD OF SOMATOTROPIN NATURATION

[75] Inventors: Larry A. Bentle, St. Charles; James W. Mitchell; Stephen B. Storrs, both of St. Louis, all of Mo.

[73] Assignee: Monsanto Company, St. Louis, Mo.

Reexamination Request:
No. 90/002,454, Sep. 26, 1991

Reexamination Certificate for:
Patent No.: 4,652,630
Issued: Mar. 24, 1987
Appl. No.: 704,677
Filed: Feb. 22, 1985

[51] Int. Cl.$^5$ .................... C07K 1/14; C07K 3/12; C07K 1/02
[52] U.S. Cl. .................... 530/344; 530/420; 930/120
[58] Field of Search .............. 530/344, 399, 419, 420

[56] References Cited

U.S. PATENT DOCUMENTS

| | | | |
|---|---|---|---|
| 4,511,502 | 4/1985 | Builder et al. | 530/422 |
| 4,512,922 | 4/1985 | Jones et al. | 530/422 |
| 4,518,526 | 5/1985 | Olson | 530/422 |
| 4,572,798 | 2/1986 | Koths et al. | 530/351 |
| 4,620,948 | 11/1986 | Builder et al. | 530/419 |
| 4,623,716 | 11/1986 | Stevenson et al. | 530/333 |
| 4,745,069 | 5/1988 | Mayne et al. | 435/320 |

FOREIGN PATENT DOCUMENTS

0114506 8/1984 European Pat. Off.
WO83/04418 12/1983 PCT Int'l Appl.
WO84/03711 9/1984 PCT Int'l Appl.

OTHER PUBLICATIONS

Dellacha et al., (1964), "Purification of Bovine Growth Hormone", Journal of Biological Chemistry, 238(8), pp. 1515–1520.
Lemay et al., (1974), "Stability of Secretory Granules Containing Growth Hormone and Prolactin from Bovine Anterior Pituitary Gland", Canadian Journal of Biochemistry, 52, pp. 327–331.
Marston et al., Biotechnology, pp. 800–804 (1984).
Emtage et al., Proc. Natl. Acad. Sci. USA, vol. 80, pp. 3671–3675 (1983).
Pace, C. N., CRC Critical Reviews in Biochemistry, pp. 1–43 (1975).
Marston et al., Methods in Enzymology, vol. 182, pp. 264–276 (1990).
Condliffe et al., Growth and Growth Hormone, I.C.S. No. 158 pp. 38–44 (1968).
Epstein et al., Cold Spring Harbor Symposium, 28: 439–449 (1963).
Edelhoch et al., The Journal of Biological Chemistry, vol. 241, No. 2, (1966) pp. 458–463.
Edelhock et al., The Journal of Biological Chemistry, vol. 241, No. 22, (1966) pp. 5205–5212.
Ghelis and Yon, "Protein Folding", Academic Press (1982), pp. 223–295.
Kenten et al., Proc. Natl. Acad. Sci. USA, vol. 81 (1984), pp. 2955–2959.
Cabilly et al., Proc. Nat. Acad. Sci. USA, vol. 81 Jun. 1984, pp. 3273–3277.
Schoner et al., Proc. Natl. Acad. Sci. USA, vol. 81 Sep. 1984, pp. 5403–5407.
Schoner et al. Bio/Technology, Feb. 1985, pp. 151–154.
Marston et al., Biochem. Soc. Trans., vol. 13, No. 6 (1985), p. 1035.
Marston et al., Biochem. Soc. Trans., vol. 16, No. 2 (1988), pp. 112–115.

Primary Examiner—Jeffrey Edwin Russel
Attorney, Agent, or Firm—Stanley M. Tarter

[57] ABSTRACT

Methods of solubilization and naturation of somatotropin protein from refractile bodies of host cells are disclosed. The solubilization methods embrace the discovery that an aqueous urea solution can be effectively used to solubilize refractile bodies containing such somatotropin protein. Surprisingly, it has been further found that once solubilized, such somatotropin protein can be natured in the urea solution by contacting the solution with a mild oxidizing agent for a time sufficient to result in the formation of the disulfide protein. Naturation can efficiently occur even at high protein concentration, in an impure preparation and in the absence of reducing agent.

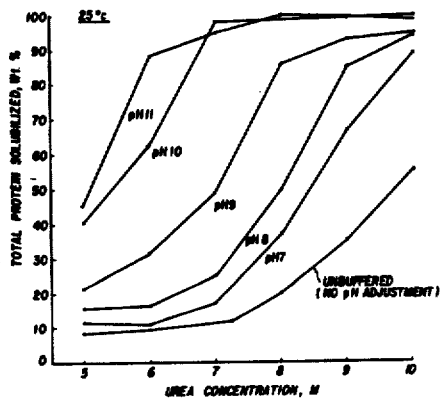

B1 4,652,630

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 7, lines 23–44:

In the present invention solubilization of significant quantities of somatotropin protein was attained by increasing or decreasing the pH of the aqueous urea solution. While the unexpected effect of adjusting the solution pH to a more acidic or alkaline pH will be evident from the following examples, adjustment to an alkaline pH is preferred since the naturation step, specifically the oxidation of the reduced monomer, is base catalyzed. The pH of the solution may be made more alkaline by addition of a suitable base such as sodium hydroxide. As the refractile bodies dissolve, the pH of the solution may decrease, requiring the periodic addition of more base to maintain alkaline conditions. *As illustrated by the data of FIG. 2, the pH of the solution may be above 9, e.g., 9.5 or higher, preferably 9.5 to 12 and most preferably from about 10 to 11.* Refractile bodies have been completely solubilized at concentrations as high as 60 mg/ml or more. Moreover, solubilization has been achieved at urea concentrations as low as 1.0M *and at urea concentrations as high as 7.5M as shown in FIG. 2 and 10M as shown in FIG. 1.* The solubilization conditions required (i.e., urea concentration, amount of urea solution used relative to the amount of refractile bodies and the solution pH) will depend on the particular refractile body composition and the amount of refractile bodies to be solubilized.

Column 8, lines 44–54:

Formation of disulfide bonds in proteins is proposed to occur by a base catalyzed free radical mechanism such as that described by March in Adv. Organic Chemistry, McGraw Hill (1977). Being base catalyzed, the oxidation step is preferably carried out at alkaline pH. While the oxidation reaction forming the disulfide bonds will proceed at pH greater than about 7, an operating pH above the pK for a protein sulfhydryl group (~8.4) is preferred. *The examples which follow illustrate the practice of the invention at pH's of 10.5 and 11.* Specifically, an operating pH between about 9 and 12 is preferred. Thus, one may use a pH of 9.5 or higher. If a buffer is used, Tris(hydroxymethyl)amino methane is preferred.

Column 9, lines 29–38:

In the case of N-methionyl bovine somatotropin, a urea concentration during naturation of between about [4M and 5M is preferred] *4M and 6M and particularly between about 4M and 5M is preferred as illustrated by the data in FIG. 3.* Naturation appears optimal at about 4.5M with decreased monomer recovery and increased aggregate formation at both higher and lower urea concentrations. Accordingly, if 7.5M urea is used for solubilization, rapid dilution to 4.5M urea with distilled water or a suitable buffer such as Tris is preferred in the absence of reducing agent to minimize oxidation at the higher non-optimal urea concentration. *When a urea concentration of 4M–6M is used for solubilization, such dilution may not be necessary.*

Column 9, lines 39–49:

In the case of N-methionyl porcine somatotropin, which differs from MBS in 18 amino acids, a urea concentration during reactivation of between 2.5M and 3.5M is preferred. Naturation appears optimal at about 3M urea with decreased monomer recovery and increased aggregate formation at both higher and lower urea concentrations. Likewise, rapid dilution from 7.5M to 3M urea with good mixing, a suitable buffer such as Tris is preferred in the absence of reducing agent to minimize renaturation at higher non-optimal urea concentrations. *When a urea concentration of 2.5M–3.5M is used for solubilization, no such dilution may be necessary.*

AS A RESULT OF REEXAMINATION, IT HAS BEEN DETERMINED THAT:

Claims 10–17 are cancelled.

Claims 1, 3, 4, 9 and 18–20 are determined to be patentable as amended.

Claims 2, 5–8, and 21–24, dependent on an amended claim, are determined to be patentable.

New claims 25–51 are added and determined to be patentable.

1. A method for solubilization and naturation of somatotropin protein from refractile bodies of a host cell containing said protein, which method comprises contacting said bodies with an effective amount and concentration of an aqueous urea solution at a pH effective to accomplish solubilization of said protein and then contacting the solution containing said protein with a mild oxidizing agent *at a pH of 9.5 or higher* for a time sufficient to form intramolecular disulfide bonds between cysteine residues contained in said somatotropin protein.

3. The method of claim 1 in which the [naturation] *solubilization* is conducted [at a pH above 9] *at a urea concentration of 1M to 10M.*

4. The method of claim 1 in which the naturation is conducted at a pH [between about 9 and 12] *up to about 12.*

9. The method of claim 8 in which the naturation is conducted at a urea concentration between about 3 and 5M; a temperature above the freezing point of the solution and below about 25° C.; and a pH [between about 9 and 12] *up to about 12.*

18. A method for naturation of somatotropin protein which comprises contacting a urea solution of said protein with a mild oxidizing agent for a time sufficient to form intramolecular disulfide bonds between cysteine residues contained in said somatotropin protein, said naturation *being* conducted at a pH [above 9] *of 9.5 or higher.*

19. The method of claim 18 in which the naturation is conducted at a pH [between about 9 and 12] *up to about 12.*

20. The method of claim 18 in which the naturation is conducted at a temperature above the freezing point of the solution and below about 25° C. *and in a urea concentration of 1 to 7.5M.*

*25. A method for naturation of bovine somatotropin protein which comprises contacting an aqueous urea solution of said protein with a mild oxidizing agent for a time sufficient to form intramolecular disulfide bonds between cysteine residues contained in said somatotropin protein, said naturation being conducted at a pH of 9.5 or higher.*

*26. The method of claim 25 in which said pH is between about 10.5 and 11.*

*27. The method of claim 25 in which the concentration of urea in said solution is between about 4 and 6M.*

*28. A method for naturation of bovine somatotropin protein which comprises contacting an aqueous urea solution of said protein with a mild oxidizing agent at a temperature above the freezing point of the solution and below about 25° C. for a time sufficient to form intramolecular disulfide bonds between cysteine residues contained in said somatotropin protein, the concentration of urea in said solution being between about 4 and 6M and said naturation being conducted at a pH between about 10.5 and 11.*

*29. A method for solubilization and naturation of bovine somatotropin protein from refractile bodies of a host cell culture containing said protein, which method comprises*

*a) contacting said refractile bodies with an aqueous solution of urea at a concentration, temperature and pH effective to solubilize said protein; and*

*b) naturizing said solubilized protein by contacting the solution containing said protein with a mild oxidizing agent for a time sufficient to form intramolecular disulfide bonds between cysteine residues contained in said somatotropin protein,*

*said solubilization being conducted at a urea concentration of 1 to 7.5M, said naturation being conducted at a urea concentration of between about 4 and 6M, and said solubilization and naturation each being conducted at a pH of 9.5 or higher and at a temperature above the freezing point of said solution and below about 25° C.*

*30. The method of claim 29 wherein said solubilization is conducted at a urea concentration of between about 4 and 6M.*

*31. The method of claim 30 wherein said solubilization and naturation are conducted at substantially the same urea concentration.*

*32. The method of claim 31 wherein said urea concentration is about 4.5M.*

*33. The method of claim 29 wherein said solubilization and naturation are conducted at a pH up to about 12.*

*34. The method of claim 29 wherein said solubilization and naturation are conducted at substantially the same pH.*

*35. The method of claim 34 wherein said pH is between about 10.5 and 11.*

*36. The method of claim 29 wherein said solubilization and naturation are conducted under substantially the same conditions of urea concentration, pH and temperature.*

*37. The method of claim 36 wherein said solubilization and naturation are conducted in an aqueous solution of urea at a concentration of about 4.5M, a temperature of about 4° C. and a pH of about 11.*

*38. A method for solubilization and naturation of procine somatotropin protein from refractile bodies of a host cell culture containing said protein, which method comprises*

*a) contacting said refractile bodies in an aqueous solution of urea at a concentration, temperature and pH effective to solubilize said protein; and*

*b) naturizing said solubilized protein by contacting the solution containing said protein with a mild oxidizing agent for a time sufficient to form intramolecular disulfide bonds between cysteine residues contained in said somatotropin protein,* said solubilization being conducted at a urea concentration of 1 to 7.5M, said naturation being conducted at a urea concentration of 2.5 to 3.5M, and said solubilization and naturation each being conducted at a pH of 9.5 or higher and at a temperature above the freezing point of said solution and below about 25° C.

*39. The method of claim 38 wherein said solubilization is conducted at a urea concentration of 2.5 to 3.5M.*

*40. The method of claim 38 wherein said solubilization and naturation are conducted at substantially the same urea concentration.*

*41. The method of claim 40 wherein said urea concentration is about 3M.*

*42. The method of claim 38 wherein said solubilization and naturation are conducted under substantially the same conditions of urea concentration, pH and temperature.*

*43. The method of claim 42 wherein said solubilization and naturation are conducted in an aqueous solution of urea at a concentration of about 3M, a temperature of about 4° C. and a pH of about 11.*

*44. A method for naturation of bovine somatotropin protein which comprises contacting an aqueous urea solution containing said protein with a mild oxidizing agent for a time sufficient to form intramolecular disulfide bonds between cysteine residues contained in said somatotropin protein, said naturation being conducted at a pH of 9.5 or higher at a urea concentration of 4 to 6M, and at a temperature above the freezing point of said solution and below about 25° C.*

*45. The method of claim 44 wherein said urea concentration is about 4.5M.*

*46. The method of claim 44 wherein the pH is up to about 12.*

*47. The method of claim 44 wherein said pH is between about 10.5 and 11.*

*48. The method of claim 44 wherein said naturation is conducted in an aqueous solution of urea at a concentration of about 4.5M, a temperature of about 4° C. and a pH of about 11.*

*49. A method for naturation of porcine somatotropin protein which comprises contacting an aqueous urea solution containing said protein with a mild oxidizing agent for a time sufficient to form intramolecular disulfide bonds between cysteine residues contained in said somatotropin protein, said naturation being conducted at a pH of 9.5 or higher at a urea concentration of 2.5 to 3.5M, and at a temperature above the freezing point of said solution and below about 25° C.*

*50. The method of claim 49 wherein said urea concentration is about 3M.*

*51. The method of claim 49 wherein said naturation is conducted in an aqueous solution of urea at a concentration of about 3M, a temperature of about 4° C. and a pH of about 11.*

* * * * *